US007786337B2

(12) United States Patent
Brown et al.

(10) Patent No.: US 7,786,337 B2
(45) Date of Patent: Aug. 31, 2010

(54) OLEFIN OLIGOMERIZATION PROCESS

(75) Inventors: Stephen Harold Brown, Bernardsville, NJ (US); John Stephen Godsmark, Grez Doiceau (BE); Georges Maria Karel Mathys, Bierbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 699 days.

(21) Appl. No.: 11/596,170

(22) PCT Filed: May 26, 2005

(86) PCT No.: PCT/EP2005/005784

§ 371 (c)(1),
(2), (4) Date: Nov. 10, 2006

(87) PCT Pub. No.: WO2005/118513

PCT Pub. Date: Dec. 15, 2005

(65) Prior Publication Data

US 2007/0173676 A1    Jul. 26, 2007

(30) Foreign Application Priority Data

Jun. 1, 2004    (GB) ................................. 0412151.3

(51) Int. Cl.
*C07C 2/24*    (2006.01)

(52) U.S. Cl. ...................... 585/533; 585/514; 585/517; 585/520; 585/529

(58) Field of Classification Search ................. 585/514, 585/517, 520, 529, 533
See application file for complete search history.

(56) References Cited

U.S. PATENT DOCUMENTS

| 3,960,978 | A |   | 6/1976 | Givens et al. | ........ 260/683.15 R |
| 4,021,502 | A |   | 5/1977 | Plank et al. | ......... 260/683.15 R |
| 4,520,221 | A |   | 5/1985 | Hsia Chen | .................. 585/517 |
| 4,675,463 | A |   | 6/1987 | Glivicky et al. | ............. 585/820 |
| 4,919,896 | A |   | 4/1990 | Harandi et al. | .............. 422/142 |
| 5,157,201 | A | * | 10/1992 | Norris | ........................ 585/820 |
| 5,672,800 | A |   | 9/1997 | Mathys et al. | .............. 585/520 |
| 6,025,533 | A |   | 2/2000 | Vora et al. | ................... 585/330 |
| 6,143,942 | A |   | 11/2000 | Verrelst et al. | ............. 585/533 |
| 2002/0111523 | A1 |   | 8/2002 | Mathys et al. | |
| 2008/0039669 | A1 |   | 2/2008 | Brown et al. | |

FOREIGN PATENT DOCUMENTS

| EP | 0 746 538 | 12/1996 |
| WO | WO 94/12452 | 6/1994 |
| WO | WO 95/22516 | 8/1995 |
| WO | WO 03/035583 | 5/2003 |
| WO | WO 03/035584 | 5/2003 |
| WO | WO2005/118512 | 12/2005 |

* cited by examiner

*Primary Examiner*—In Suk Bullock
(74) *Attorney, Agent, or Firm*—Andrew B. Griffis; Leandro Arechederra, III

(57) ABSTRACT

In a process for oligomerizing an olefinic hydrocarbon feedstock, the feedstock is contacted under oligomerization conditions with (a) a first crystalline molecular sieve catalyst and (b) a second catalyst comprising a solid phosphoric acid. The first and second catalysts may be contained in separate reactors or as separate beds in a single reactor.

31 Claims, No Drawings

OLEFIN OLIGOMERIZATION PROCESS

CROSS REFERENCE TO RELATED APPLICATIONS

The present application is related by subject matter to GB Patent Application 0412139.8 filed 1 Jun. 2004 and its equivalent PCT patent application (PCT/EP05/05785), the entire contents of which applications are incorporated herein by reference.

FIELD

The present invention relates to a process for the oligomerization of olefin containing feedstocks, particularly but not exclusively a feedstock containing at least about 50 wt. % olefins.

BACKGROUND

The oligomerization of lower olefins, particularly $C_2$ to $C_6$ olefins, to produce higher molecular weight olefinic products is an important commercial process useful in, for example, the production of fuels and precursors for plasticizers, surfactants, and freeze point depressants for lubricating oils.

For example, approximately 70 units exist world wide for the purpose of oligomerizing olefins (typically mixtures of propylene and butenes) e.g., from Fluid Catalytic Cracker (FCC) unsaturated gas plants and/or steam crackers to gasoline and or distillate. These plants employ multiple reactors filled with solid phosphoric acid catalyst (sPa). SPa catalyst typically produces 500 to 1500 weight units of oligomer per weight unit of catalyst and then reaches the end of its useful life. As a result, most operators are required to shut down and reload catalyst into a reactor every 3 to 10 weeks. The reactor is taken off line, refilled with fresh catalyst, and brought back on line. Reactor turnaround for sPa catalyst is particularly difficult. During the course of use, sPa catalyst agglomerates to form a single, solid block which must be water jetted or drilled out of the reactor. Although sPa catalyst is inexpensive (currently about $2/lb), catalyst cost to produce oligomer is high compared to processes with more productive catalysts such as hydrotreating catalysts, hydrocracking catalysts, FCC catalysts, ethylbenzene and cumene catalysts, xylene isomerization catalysts, etc. due to the large quantities of sPa catalyst required and the expense associated with shutting down and restarting reactors.

For many units, sPa catalyst useful lifetime is limited by the increasing pressure drop caused by the steady catalyst agglomeration and not by loss of too much catalyst activity. Because of these problems, operators of sPa olefin oligomerization units are careful to maintain operating conditions that maximize catalyst cycle length. The rate of sPa fouling is known to increase with increasing feed olefin concentration. Many sPa operators therefore dilute the olefin feedstock with a paraffin recycle to increase catalyst lifetime. Paraffin dilution decreases the capacity of the unit by taking up space in pumps, reactors, heat exchangers and distillation towers.

One example of a process that utilizes a solid phosphoric acid oligomerization catalyst is U.S. Pat. No. 6,025,533, which describes a process for the production of heavy oligomers by a combination of dehydrogenation and oligomerization.

It is also known that zeolites can be attractive replacements for sPa catalysts because of their unique selectivities in olefin oligomerization. In addition, zeolite catalysts in light olefin oligomerization service do not swell and fuse, and the pressure drop across the unit remains small and constant throughout the full catalyst cycle. Zeolite catalyst fouling is also typically independent of feed olefin concentration.

For example, U.S. Pat. Nos. 3,960,978 and 4,021,502 disclose the conversion of gaseous olefins in the range of ethylene to pentene, either alone or in admixture with paraffins, into an olefinic gasoline blending stock by contacting the olefins with a ZSM-5 type zeolite. In addition, EP-B-746,538 discloses oligomerization of propene and butene to produce enhanced yields of the trimer using zeolites of the structure types MFI, TON, and MFS, such as ZSM-5, ZSM-22 and ZSM-57.

International Patent Publication No. WO 94/12452, published Jun. 9, 1994, discloses a process for producing a branched $C_4$-$C_5$ olefin by contacting a mixture of ethylene and a $C_3$-$C_{10}$ olefin with a molecular sieve selected from ZSM-22, ZSM-23, ZSM-35, ZSM-50 and SAPO-11 at a temperature of 200-700° C.

U.S. Pat. No. 4,919,896 describes the use of series reactors for oligomerization of olefins; a number of different zeolites, including ZSM-22, are proposed as catalysts.

U.S. Pat. No. 5,672,800 describes a process for oligomerization of $C_2$-$C_{12}$ alkene-containing feedstock having a water content of from 0.05 to 0.25 molar % over a zeolite catalyst.

U.S. Pat. No. 6,143,942 and International Patent Publication No. WO 95/22516, published Aug. 24, 1995, disclose an olefin oligomerization process comprising contacting a feed comprising at least one olefin under oligomerization conditions with a catalyst comprising at least one zeolite having a constraint index greater than 10, such as ZSM-22, and at least one zeolite having a constraint index of 2 to 10, such as ZSM-5 or ZSM-57, said zeolites being present in a proportion within the range of 10:90 to 90:10 by weight. Advantageously the two molecular sieves are in admixture but they can also be arranged in separate beds so that the feed passes through them in series. The feed can contain an inert diluent, such as a saturated hydrocarbon, in addition to said at least one olefin. For a feed comprising propene, a suitable diluent is said to be propane, advantageously in proportions of propene propane from 10:90 to 60:40, especially about 50:50 by weight.

However, not only are zeolite catalysts often expensive, but they tend to produce a different product slate than sPa catalysts when used to oligomerize olefins. For example, zeolite catalysts tend to produce more less branched products and more heavy molecules, with the product being more heavily weighted towards materials that are an integer multiple of the olefin monomer. Moreover, zeolite product carbon distribution is a strong function of conversion between 90 and 99% light olefin conversion. As conversion increases, distillate selectivities of greater than 30% can be obtained. SPa catalyst product number distribution remains nearly constant across this conversion range with less than about 10% selectivity to distillate.

In addition, zeolite catalysts can pose problems when used to oligomerize olefins under commercial, non-isothermal conditions. Thus high-olefin content (>65%) feedstocks containing propylene are among the most important feedstocks in the industry but oligomerization of these feedstocks is highly exothermic. When zeolite catalysts are used to process such feedstocks, large and unstable exotherms can develop anywhere in the reactor bed requiring reactor shutdown.

There is therefore a need for an oligomerization process in which catalyst lifetime can be improved and in which high olefin content feedstocks can be processed without diluents and without the production of uncontrollable exotherms.

SUMMARY

Accordingly, the invention resides in a process for oligomerizing an olefinic hydrocarbon feedstock, the process comprising:
(a) contacting the feedstock under olefin oligomerization conditions with a catalyst comprising crystalline molecular sieve, and
(b) contacting the feedstock under olefin oligomerization conditions with a catalyst comprising a solid phosphoric acid.

It will be understood that, since the contacting steps (a) and (b) are performed sequentially (with (a) first or with (b) first), the 'feedstock' that contacts catalyst in the second step will in fact be the initial feedstock that has already been contacted under oligomerization conditions with catalyst in the first step.

It is preferred that the crystalline molecular sieve has pores defined by unidimensional channels formed by 10-membered rings of tetrahedrally coordinated atoms. Preferred examples of such molecular sieves are TON structure type materials, such as ZSM-22; MTT structure type materials, such as ZSM-23; AEL structure type materials, such as SAPO-11; and members of the ZSM-48 family such as ZSM-48 itself.

Preferably, the olefinic hydrocarbon feedstock comprises at least about 50 wt % olefins, more preferably at least about 65 wt % olefins and most preferably at least about 70 wt % olefins.

Accordingly, a preferred embodiment of the invention also resides in a process for oligomerizing an olefinic hydrocarbon feedstock comprising at least about 50 wt. % olefins, the process comprising:
(a) contacting the feedstock under olefin oligomerization conditions with a catalyst comprising a crystalline molecular sieve having pores defined by unidimensional channels formed by 10-membered rings of tetrahedrally coordinated atoms, and
(b) contacting the feedstock under olefin oligomerization conditions with a catalyst comprising solid phosphoric acid.

Conveniently the feedstock comprises at least one olefin having about 2 to about 12 carbon atoms, preferably 2 to 6 carbon atoms, such as propylene and/or butene.

Conveniently, the hydrocarbon feedstock comprises at least about 50 wt. % olefins, such as at least about 65 wt. % olefins.

Conveniently, the crystalline molecular sieve of the first catalyst has the TON structure type.

Conveniently, the feedstock is hydrated prior to contact with the crystalline molecular sieve catalyst.

In a preferred embodiment, the contacting (a) is effected before the contacting (b).

In one embodiment, the catalysts employed in said contacting (a) and said contacting (b) comprise stacked beds in a single reactor. In another embodiment, the catalysts employed in said contacting (a) and said contacting (b) are contained in separate reactors.

DETAILED DESCRIPTION OF THE EMBODIMENTS

The present invention provides a process for oligomerizing an olefinic hydrocarbon feedstock, and in particular a feedstock containing at least 50 wt. % olefins, in which the feedstock is contacted under oligomerization conditions with (a) a first crystalline molecular sieve catalyst and (b) a second oligomerization catalyst comprising an sPa catalyst.

Conveniently, the hydrocarbon feedstock is contacted with the first crystalline molecular sieve catalyst prior to contacting with the second sPa catalyst. In conventional reactor arrangements, this means that the crystalline molecular sieve catalyst is on top of the sPa catalyst. In this way, part of the olefins in the feedstock is converted to oligomers before the feedstock contacts the sPa catalyst. The light olefin concentration in the feedstock contacting the sPa catalyst is thus lowered allowing the mixed catalyst system to operate without, or with a decreased amount, of paraffin diluent. The lowered olefin concentration also lowers the rate of sPa fouling/pressure drop build up. In addition to lowering the rate of sPa fouling/pressure drop build up, substitution of sPa with zeolite in the reactor reduces the depth of the sPa bed. Since pressure drop is a function of bed depth, the combined catalyst system further lengthens the amount of time the process can be operated before reaching the reactor pressure drop limit, compared with a process using only sPa catalyst.

In addition, placing the less active molecular sieve catalyst, e.g. ZSM-22, on top of the sPa catalyst helps maintain an isothermal reactor profile in a tubular reactor. Using a single bed of molecular sieve, such as ZSM-22, catalyst or sPa catalyst results in a significant amount of extra heat being released at the top of a tubular reactor operating to effect olefins conversion at commercially useful >90% per pass conversion. The extra heat is released at the top of the reactor because the reaction driving force is much higher there (monomer concentration is highest at the top of the tube). Providing the more active catalyst at the bottom of the reactor tube helps shift heat release from the top to the bottom of the reactor allowing more isothermal operation. This helps optimize catalyst stability and selectivity.

The use of mixed (sequential) catalyst therefore allows for the process of the present invention to process feed at higher rates and/or for longer periods of time than conventional olefin oligomerization processes.

Feedstock

The hydrocarbon feedstock used in the present process typically contains olefins having from about 2 to about 12 carbon atoms, such as from about 2 to about 6 carbon atoms. The feedstock itself may be or comprise an oligomer, such as a dimer, especially one provided by recycling a part of a product stream. In one embodiment, the feed contains propene, butenes, pentenes and/or hexenes. The process is especially applicable to propene and butene oligomerization.

The feedstock may contain greater than about 50 wt. % olefins, for example greater than about 65 wt. % olefins or greater than 70 wt. % olefins. Other suitable feedstocks include untreated refinery streams such as FCC, coker, and pygas streams as well as aromatics-containing streams, such as reformates. One particularly preferred feedstock comprises an FCC light olefin stream, which typically comprises ethane, ethylene, propane, propylene, isobutane, n-butane, butenes and pentanes. An example of such a feedstock possesses the following composition:

|  | Wt. % | Mole % |
|---|---|---|
| Ethane | 3.3 | 5.1 |
| Ethylene | 0.7 | 1.2 |
| Propane | 4.5 | 15.3 |

-continued

|  | Wt. % | Mole % |
|---|---|---|
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

In addition, the feedstock may comprise an inert diluent, for example, a saturated hydrocarbon.

Prior to oligomerization, the feedstock may be hydrated and in particular sufficient water may be added to saturate the feedstock. Conveniently, the feedstock comprises from about 0.01 to about 0.25, such as from about 0.02 to about 0.20 and for example from about 0.03 to about 0.10, molar % water based on the total hydrocarbon content of the feedstock. If desired or required, the natural water content of the feedstock may be increased, for example, by passage through a thermostatted water saturator. Since the amount of water required to saturate the feedstock will depend upon the temperature and composition of the feedstock, control of the water content may be effected by appropriate control of the temperature of the feedstock.

Crystalline Molecular Sieve Oligomerization Catalyst

In the oligomerization process of the invention, the olefinic hydrocarbon feedstock is contacted, preferably initially, with a crystalline molecular sieve catalyst. The catalyst can include any crystalline molecular sieve which is active in olefin oligomerization reactions. In one embodiment, the catalyst includes a medium pore size molecular sieve having a Constraint Index of about 1 to about 12. Constraint Index and a method of its determination are described in U.S. Pat. No. 4,016,218, which is incorporated herein by reference.

Examples of suitable medium pore size molecular sieves include those of the TON structure type (for example, ZSM-22, ISI-1, Theta-1, Nu-10, and KZ-2), those of the MTT structure type (for example, ZSM-23 and KZ-1), those of the MFI structure type (for example, ZSM-5), those of the MFS structure type (for example, ZSM-57), those of the MEL-structure type (for example, ZSM-11), those of the MTW structure type (for example, ZSM-12), those of the EUO structure type (for example, EU-1), those of the AEL structure type (for example, SAPO-11), members of the ferrierite family (for example, ZSM-35) and members of the ZSM-48 family of molecular sieves (for example, ZSM-48 itself). In this specification, the term "structure type" is used in the sense described in the Structure Type Atlas, Zeolites 17, 1996.

Preferred molecular sieves are those having pores defined by unidimensional channels formed by 10-membered rings of tetrahedrally coordinated atoms, such as molecular sieves having the TON structure type. Thus, unidimensional 10 ring molecular sieves are unusually selective for the formation of dimers when used in light olefin oligomerization service at high monomer conversion. Limiting the reaction to the conversion of monomers to dimers limits the amount of oligomerization heat release, which in turn reduces the tendency to form uncontrollable hot spots during light olefin oligomerization.

Other examples of suitable molecular sieves include offretites, ZSM-4, erionites, chabazites, ZSM-18, zeolite beta, faujasites, zeolite L, mordenites and members of MCM-22 family of molecular sieves (including, for example, MCM-22, PSH-3, SSZ-25, ERB-1, ITQ-1, ITQ-2, MCM-36, MCM-49 and MCM-56).

The crystalline molecular sieve is advantageously ZSM-22, ZSM-23, SAPO-11 or ZSM-48. ZSM-22 and its manufacture are described in, for example, U.S. Pat. No. 4,556,477 and WO 93/25475. ZSM-23 and its manufacture are described in, for example, U.S. Pat. No. 4,076,842. SAPO-11 and its manufacture are described in, for example, U.S. Pat. Nos. 4,40,871 and 6,294,493. Mixtures of two or more molecular sieves e.g., a mixture of ZSM-22 and ZSM-57, may also be used. Preferably, the molecular sieve(s) is employed in its H- or acid form.

The molecular sieve conveniently has a crystallite size up to 5 µm, such as within the range of from 0.05 to 5 µm, for example from 0.05 to 2 µm, and typically from 0.1 to 1 µm. An as-synthesized molecular sieve is advantageously converted to its acid form, for example by acid treatment, e.g., by HCl, or by ammonium ion exchange, and subsequent calcination before use in the process of the invention. The calcined materials may be post-treated, such as by steaming. Although the invention will be described with reference to aluminosilicate zeolites, it is possible to use, as is known in the art, a material in which silicon and aluminum have been replaced in whole or in part by other elements, silicon more especially by germanium or phosphorus and aluminum more especially by boron, gallium, chromium and iron, materials containing such replacement lattice elements also being termed zeolites, and the term being used in the broader sense in this specification.

The molecular sieve may be supported or unsupported, for example in powder form, or used as an extrudate with an appropriate binder. Where a binder is employed, the binder is preferably present in an amount such that the oligomerization catalyst contains between about 2 and about 80 wt % of the molecular sieve. The binder is conveniently a metal oxide, such as alumina.

Solid Phosphoric Acid Oligomerization Catalyst

The second catalyst used in the oligomerization process of the invention is a solid phosphoric acid (sPa) catalyst. As previously mentioned, the sPa catalyst refers to a solid catalyst that contains as a principal ingredient an acid of phosphorus such as ortho-pyro- or tetra-phosphoric acid. The sPa catalyst preferably comprises a carrier. Thus, the catalyst is normally formed by mixing the acid of phosphorus with a solid carrier, preferably siliceous, to form a wet paste. This wet paste may be calcined and then crushed to yield catalyst particles where the paste may be extruded or pelleted prior to calcining to produce more uniform catalyst particles.

The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives (when present) preferably comprises about 15-30% of the catalyst, with the remainder being the phosphoric acid. The additive (when present) may, for example, comprise about 3-20% of the total carrier material. However, variations from this such as a lower phosphoric acid content are possible. Further details as to the composition and production of sPa catalysts may be obtained from U.S. Pat. Nos. 3,050,472; 3,050,473, and 3,132,109 and from other references.

Oligomerization Reaction System

The crystalline molecular sieve zeolite catalyst may be provided in a separate bed or a separate reactor. Preferably it is upstream of the sPa oligomerization catalyst or may be provided as a top layer on the sPa oligomerization catalyst. In the latter case, if crystalline molecular sieve loss minimization is considered important, a small zone of inert material, such as alumina balls, can be used to separate the crystalline molecular sieve from the sPa oligomerization catalyst.

In one practical embodiment, the bottom of an oligomerization reactor is loaded with sPa catalyst and the top of the reactor is loaded with a unidimensional, 10-ring molecular sieve catalyst. In operation, the unidimensional, 10-ring molecular sieve catalyst selectively converts feedstock monomers to dimers before the feedstock contacts the sPa catalyst bed. The feedstock, having a reduced concentration of light olefins, particularly propylene, is then converted to the desired distribution of higher oligomers over the downstream sPa catalyst. The limited amount of heat released by the selective dimerization over the molecular sieve catalyst reduces the amount of heat required to be removed with conventional tubular or chamber reactors. Because the tendency to form uncontrollable exotherms is greatly reduced, feedstocks with higher olefin concentrations can be processed.

An undesirable consequence of most mixed catalyst systems in fixed-bed or tubular reactors is the added burden upon the operator of separating the catalysts at the end of the catalyst life, especially where economically viable use of one or each catalyst requires regeneration and re-use. Surprisingly, separation of the oligomerization catalysts of the present invention has been found not to be a problem with molecular sieve (zeolite)/sPa mixtures.

Thus the sPa catalyst agglomerates into a solid mass during operation. This solid mass has been found to solve the separation problem. The zeolite catalyst may be vacuumed from the top of the reactor. The solidified sPa catalyst is not removed by the vacuum. When no more catalyst exits the reactor, conventional drilling or water-jetting procedures are begun to remove the solid sPa catalyst. Any molecular sieve catalyst stuck at the top of the sPa bed is also drilled out and discarded.

Conveniently, the reactor system comprises from about 25 to about 95 vol %, more preferably from about 50 to about 90 vol %, of the molecular sieve based on the total volume of the molecular sieve and the sPa in the overall catalyst system.

Oligomerization Conditions

The reaction conditions used in the molecular sieve olefin oligomerization step (a) of the present process are not narrowly defined and may be the same as or different from those of the sPa oligomerization step (b). However, preferred operating temperatures for the olefin oligomerization are generally between about 80° C. and about 350° C. Toward and above the upper end of the range, deoligomerization rates increase and may predominate over the oligomerization reaction, providing an upper limit to practical operation. More typically, the reaction temperature is in the range of about 130° C. to about 320° C., such as between about 135° C. and about 310° C., for example between about 160° C. and about 270° C.

The pressure is conveniently in the range of about 400 psig to about 4000 psig (2860 to 27680 kPaa), such as from about 500 psig to about 1500 psig (3550 to 10440 kpaa). The olefin weight hourly space velocity is advantageously in the range of from about 0.1 $hr^{-1}$ to about 20 $hr^{-1}$, such as from about 0.5 $hr^{-1}$ to about 5 $hr^{-1}$.

In one embodiment, contacting step (a) is conducted at a temperature of 80-350° C.; an olefin weight hourly space velocity of 0.1-20 $hr^{-1}$; and a pressure of 2860-27680 kpaa.

In another embodiment, which may be performed in combination with the embodiment mentioned immediately above, contacting step (b) is conducted at a temperature of 130-320° C.; an olefin weight hourly space velocity of 0.5-5 $hr^{-1}$; and a pressure of 3550-10440 kPaa.

The invention will now be more particularly described with reference to the following Examples.

Example 1

A steam thermosyphon-controlled tubular reactor with 1.7 inch (4.3 cm) internal diameter and 30 foot (9.1 m) long tubes is loaded with 9.5 feet (2.9 m) of sPa catalyst, 0.5 feet (15 cm) of alumina balls, and 18 feet (5.5 m) of ZSM-22 catalyst. The feed to the reactor comprises 47% propylene, 3% butenes, 12% butanes, 2% ethane, and 36% propane. The feed is pre-heated to 170° C. and pressurized to 72 bar gauge (7300 kPa) and is fed to the reactor so as to contact the layer of ZSM-22 catalyst before contacting the sPa catalyst. The temperature of the steam in the reactor jacket is increased with time in order to maintain a target olefin conversion of 90-99%.

The nonene product of the reaction is found to contain a similar quantity (5-7 wt %) of triple branched isomers to that expected for an sPa catalyst alone as compared with the 9-10 wt % of triple branched nonene isomers expected for ZSM-22 alone. The nonene product of the reaction is also found to contain a similar quantity of linear and mono-branched nonenes (3 and 27% respectively) to that expected for a ZSM-22 catalyst alone as compared to the values of linear and mono-branched nonenes expected for sPa alone (0 and 7% respectively). In addition, the reaction is accompanied by a uniform exotherm varying less than plus or minus 5 degrees C. even at a conversion rate of 99%. Moreover, the stacked catalyst is exhibits a stability about five times greater than that of an sPa catalyst alone. The catalyst can be drilled from the reactor at the end of the run. Expensive water jetting is not required as is typically the case in this type of reactor employing a sPa catalyst alone.

Example 2

The experiment of Example 1, at 2 weeks on stream, had produced 260 tonne product/tonne total catalyst. At this time, the reactor was operating at a temperature of 220° C. and a pressure of 7300 kPa. At a conversion rate of 93%, the product comprised the following, in wt %

$C_6$-7.0
$C_7$-8.3
$C_8$-8.2
$C_9$-48.2
$C_{10}$-10.8
$C_{11}$-3.9
$C_{12}$-8.6
$C_{13}$-2.2
$C_{14+}$-2.8

In contrast, under the same conditions, a catalyst containing ZSM-22 alone gives an average $C_6$ of 37.4 wt %, $C_9$ of 23.4 wt %, $C_{12}$ of 10.6 wt % and 12% $C_{13}$+ ($C_{13}$+ gets only fuel value), whereas a catalyst containing sPa alone gives an average $C_6$ of 2 wt %, $C_9$ of 56 wt %, $C_{12}$ of 11.5 wt % and 4.5% $C_{13}$+. Thus the stacked bed gives sPa type selectivity with the potential to get zeolite type lifetimes.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

The invention claimed is:

1. A process for oligomerizing olefinic hydrocarbon feedstocks, the process comprising:
    (a) contacting a first feedstock under olefin oligomerization conditions with a catalyst comprising crystalline molecular sieve to form a second feedstock, and
    (b) contacting the second feedstock under olefin oligomerization conditions with a catalyst comprising solid phosphoric acid.

2. The process of claim 1 wherein the crystalline molecular sieve has pores defined by unidimensional channels formed by 10-membered rings of tetrahedrally coordinated atoms.

3. The process of claim 2 wherein the crystalline molecular sieve comprises a TON material.

4. The process of claim 3 wherein the crystalline molecular sieve comprises ZSM-22.

5. The process of claim 2 wherein the crystalline molecular sieve comprises a MTT material.

6. The process of claim 5 wherein the crystalline molecular sieve comprises ZSM-23.

7. The process of claim 2 wherein the crystalline molecular sieve comprises a material selected from the group consisting of AEL materials and materials of the ZSM-48 family of molecular sieves.

8. The process of claim 7 wherein the crystalline molecular sieve comprises a material selected from the group consisting of SAPO-11 and ZSM-48.

9. The process of claim 1 wherein the hydrocarbon feedstocks comprise at least one olefin having about 2 to about 12 carbon atoms.

10. The process of claim 9 wherein the hydrocarbon feedstocks comprise at least one olefin having about 2 to about 6 carbon atoms.

11. The process of claim 1 wherein the hydrocarbon feedstocks comprise at least one olefin selected from the group consisting of propylene, butenes and mixtures thereof.

12. The process of claim 1 wherein said contacting (a) is conducted at conditions including a temperature ranging from about 80° C. (176° F.) to about 350° C. (662° F.); an olefin weight hourly space velocity ranging from about 0.1 hr$^{-1}$ to about 20 hr$^{-1}$ and a pressure ranging from about 2,860 kPaa (400 psig) to about 27,680 kPaa (4000 psig).

13. The process of claim 1 wherein said contacting (b) is conducted at conditions including a temperature ranging from about 130° C. (266° F.) to about 320° C. (608° F.); an olefin weight hourly space velocity ranging from about 0.5 hr$^{-1}$ to about 5 hr$^{-1}$ and a pressure ranging from about 3,550 kPaa (500 psig) to about 10,440 kPaa (1500 psig).

14. The process of claim 1 wherein the catalysts employed in said contacting (a) and said contacting (b) comprise stacked beds in a single reactor.

15. The process of claim 1 wherein the catalysts employed in said contacting (a) and said contacting (b) are contained in separate reactors.

16. A process for oligomerizing olefinic hydrocarbon feedstocks comprising at least about 50 wt. % olefins, the process comprising:
    (a) contacting a first feedstock under olefin oligomerization conditions with a catalyst comprising a crystalline molecular sieve having pores defined by unidimensional channels formed by 10-membered rings of tetrahedrally coordinated atoms to form a second feedstock, and
    (b) contacting the second feedstock under olefin oligomerization conditions with a catalyst comprising solid phosphoric acid.

17. The process of claim 16 wherein the crystalline molecular sieve comprises a TON material.

18. The process of claim 17 wherein the crystalline molecular sieve comprises ZSM-22.

19. The process of claim 16 wherein the crystalline molecular sieve comprises a MTT material.

20. The process of claim 19 wherein the crystalline molecular sieve comprises ZSM-23.

21. The process of claim 16 wherein the crystalline molecular sieve comprises a material selected from the group consisting of AEL materials and materials of the ZSM-48 family of molecular sieves.

22. The process of claim 21 wherein the crystalline molecular sieve comprises a material selected from the group consisting of SAPO-11 and ZSM-48.

23. The process of claim 16 wherein the hydrocarbon feedstocks comprise at least about 65 wt. % olefins.

24. The process of claim 23 wherein the hydrocarbon feedstocks comprise at least about 70 wt. % olefins.

25. The process of claim 16 wherein the hydrocarbon feedstocks comprise at least one olefin having about 2 to about 12 carbon atoms.

26. The process of claim 25 wherein the hydrocarbon feedstocks comprise at least one olefin having about 2 to about 6 carbon atoms.

27. The process of claim 26 wherein the hydrocarbon feedstocks comprises at least one olefin selected from the group consisting of propylene, butenes, and mixtures thereof.

28. The process of claim 16 wherein said contacting (a) is conducted at conditions including a temperature ranging from about 80° C. (176° F.) to about 350° C. (662° F.); an olefin weight hourly space velocity ranging from about 0.1 hr$^{-1}$ to about 20 hr$^{-1}$ and a pressure ranging from about 2,860 kPaa (400 psig)) to about 27,680 kPaa (4000 psig).

29. The process of claim 16 wherein said contacting (b) is conducted at conditions including a temperature ranging from about 130° C. (266° F.) to about 320° C. (608° F.); an olefin weight hourly space velocity ranging from about 0.5 hr$^{-1}$ to about 5 hr$^{-1}$ and a pressure ranging from about 3,550 kPaa (500 psig) to about 10,440 kPaa (1500 psig).

30. The process of claim 16 wherein the catalysts employed in said contacting (a) and said contacting (b) comprise stacked beds in a single reactor.

31. The process of claim 16 wherein the catalysts employed in said contacting (a) and said contacting (b) are contained in separate reactors.

* * * * *